US012117402B2

(12) United States Patent
Reardon et al.

(10) Patent No.: US 12,117,402 B2
(45) Date of Patent: Oct. 15, 2024

(54) BIOLUMINESCENT SENSOR FOR ISOTHIOCYANATES

(71) Applicant: The United States of America, as represented by the Secretary of Agriculture, Washington, DC (US)

(72) Inventors: Catherine L. Reardon, Walla Walla, WA (US); Kristin M. Trippe, Philomath, OR (US); Viola Manning, Philomath, OR (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 372 days.

(21) Appl. No.: 17/386,917

(22) Filed: Jul. 28, 2021

(65) Prior Publication Data

US 2023/0030639 A1 Feb. 2, 2023

(51) Int. Cl.
| | | |
|---|---|---|
| *G01N 21/76* | (2006.01) | |
| *C12N 1/20* | (2006.01) | |
| *C12Q 1/02* | (2006.01) | |
| *C12Q 1/6897* | (2018.01) | |
| *C12R 1/39* | (2006.01) | |
| *G01N 1/28* | (2006.01) | |
| *G01N 33/24* | (2006.01) | |
| *G01N 33/50* | (2006.01) | |

(52) U.S. Cl.
CPC ............ *G01N 21/763* (2013.01); *C12N 1/20* (2013.01); *C12Q 1/02* (2013.01); *C12Q 1/6897* (2013.01); *G01N 1/28* (2013.01); *G01N 33/24* (2013.01); *G01N 33/5097* (2013.01); *C12R 2001/39* (2021.05)

(58) Field of Classification Search
None
See application file for complete search history.

(56) References Cited

FOREIGN PATENT DOCUMENTS

EP 1370862 B1 12/2005

OTHER PUBLICATIONS

Karanikolopoulou et al., "Current Methods for the Extraction and Analysis of Isothiocyanates and Indoles in Cruciferous Vegetables", Analytica, vol. 2, pp. 93-120. (Year: 2021).*
Hogaboam, O. L., 'Development of a Bioluminescent Sensor of Isothiocyanates through Genetic Modification of Pseudomonas fluorescens and Validation on Crude Plant Materials', Honors College Thesis, Oregon State University Honors College, 2020, pp. 1-29.
NCBI, GenBank Accession No. CP067022. I, 'Pseudomonas cannabina pv. alisalensis strain MAFF 301419 chromosome, complete genome', Jan. 11, 2021.
Tang, P. et al., 'Highly sensitive colorimetric paper sensor for methyl isothiocyanate (MITC): Using its toxicological reaction', Sensors and Actuators B, 2018, vol. 261, pp. 178-187.
Peru Ga, A. et al., 'Determination of methylisothiocyanate in soil and water by HS-SPME followed hy GC-MS-MS with a triple quadrupole', Anal. Bioanal. Chem., 2014, vol. 406, pp. 5271-5282.
International Search Report dated Nov. 16, 2022.

* cited by examiner

*Primary Examiner* — Michelle F. Paguio Frising
*Assistant Examiner* — Grant C Currens
(74) *Attorney, Agent, or Firm* — John D. Fado; Mark D. McNemar

(57) ABSTRACT

Disclosed are isothiocyanate (ITC)-detecting biosensors that utilize recombinant host cells containing an ITC responsive genetic element such as a saxA promoter, operably linked with a reporter element, such as a luxCDABE operon or ilux operon. Such biosensors can detect the presence of diverse ITCs in samples such as plant extracts, biofumigated soils and seed meal amended soils.

19 Claims, 13 Drawing Sheets

Specification includes a Sequence Listing.

SEQUENCE LISTING

<160> NUMBER OF SEQ ID NOS: 1

<210> SEQ ID NO 1
<211> LENGTH: 691
<212> TYPE: DNA
<213> ORGANISM: Artificial Sequence
<220> FEATURE:
<223> OTHER INFORMATION: Chemically Synthesized

```
<400> SEQUENCE: 1
catcactgac ataaagcact tctggcctga aacgaacgta agggaagcgt cgagcaaact        60
cttcccgcgc tgcccagtga gtggttgctt ctctgccatc aagcagcccg gcatctccta       120
gcacgaatgc tcccaggcac aacccgacca tgagcttgcc ttgcgcgttg gcaagctgaa       180
gggctttgac aagcggtgca gaggctgcaa cccattgatc accccacgcc ggaatgacaa       240
tgacgtcgca cgcttccatc agttccagac catgagtgac ttgcagtccg atgccttggt       300
cgctgcttat cattcccggc gactcggcgc agtaactgat ctcgtagtga ggttcatcag       360
gtgcggactg agccgttccc agcactacgc ctggcaccga aagatggaac aggctgacgc       420
ccttgaaagc cagaacagca acacgtatgg attgcatcag acagcctcgg atttgctgtg       480
tctatggagt gcgcaggaac tatgagtaag cgctcacagt gacttgtttt gaggggcggg       540
ggaggtaggg gggcatcacc gcctcatcac acatttcggg cgacgcagac acttggcccg       600
attatatcga aatatgtcat tcaggccact gtctggcctc aaggcattgg gcaacaataa       660
tgttctcgat gtatcgacag gatcaactcc a                                     691
```

BIOLUMINESCENT SENSOR FOR ISOTHIOCYANATES

SEQUENCE LISTING

The instant application contains a Sequence Listing which has been submitted via EFS-Web as ASCII compliant text file format (.txt), and is hereby incorporated by reference in its entirety. The ASCII file was 07/25/2021, is named Sequence Listing 009520 ST25.txt, and has 1.298 bytes.

BACKGROUND OF THE INVENTION

Field of Invention

The present disclosure provides isothiocyanate (ITC)-detecting biosensors that utilize recombinant host cells containing an ITC responsive genetic element such as a saxA promoter, operably linked with a reporter element, such as a luxCDABE operon. Such biosensors can detect the presence of diverse ITCs in samples such as plant extracts, biofumigated soils and seed meal amended soils.

Background

Isothiocyanates (ITCs) are natural compounds derived from cruciferous plants and are used to control plant pests and pathogens in agricultural soils. Isothiocyanates are formed by the hydrolysis of glucosinolates (GLSs; β-D-thioglucoside-N-hydroxysulfates) and reflect the chemical structure of the parent GLS. The composition and concentration of the GLSs, and resulting ITCs, vary depending on species, tissue type, developmental stage, and environmental conditions (Bellostas et al, J. Sci. Food Agr., (2007) 87(8): 1586-1594). Farmers exploit the antimicrobial and antinematicidal properties of ITC-producing plants by cover cropping or amending soils with seed meal of cruciferous plants, a process known as biofumigation. Although biofumigation is typically beneficial, ITCs can also inhibit seed germination and root growth, and produce leaf damage upon direct contact (Urbancsok et al, Int. J. Mol. Sci., (2017), 18(11): 2372). Given the variable levels of ITCs produced by plants and their relative persistence in the soil, the ability to detect ITCs and determine ITC concentrations is important to growers interested in cover cropping or seed meal amendments with cruciferous plants.

Current methods of quantifying ITCs in soil involve complicated analyses, including approaches such as spectroscopic analysis of products following reaction of ITCs with dithiols (such as 1,2-benzenedithiol), or using high performance liquid chromatography (HPLC) following extraction of ITCs with methanol (Morra and Kirkegaard, Soil Biol. Biochem., (2002) 34(11): 1683-1690). Each of these approaches requires specialized equipment and skilled technicians. We sought to develop a test more easily performed and requiring less expertise. As described herein, we have developed a biosensor for ITCs utilizing a genetically modified bacterium to address these issues with the current technology.

SUMMARY OF THE INVENTION

The present disclosure provides multiple embodiments including a biologically based test system for the detection of isothiocyanates (ITC) in samples, comprising a genetically modified microbe having a detectable indicator operably linked to an ITC-responsive promoter, wherein the detectable indicator is induced in the presence of an ITC. In some embodiments, the genetically modified microbe is an ITC-resistant bacterium such as *Pseudomonas fluorescens*. In some embodiments, the detectable indicator is a bioluminescent indicator. In particular embodiments, the bioluminescent indicator is encoded by a lux operon or an ilux operon. In some embodiments, the ITC-responsive promoter is a saxA promoter. In particular embodiments, the saxA promoter comprises a polynucleotide having a sequence at least 95% identical to SEQ ID NO: 1 or is identical to SEQ ID NO: 1. In specific embodiments, the sample comprises a soil sample, a plant sample, or a seed sample. In some embodiments, the ITC is sulforaphane, sulforaphene, metam-sodium, or allyl ITC. In most embodiments, the detectable indicator operably linked to an ITC-responsive promoter is located on a chromosome, or on a bacterial plasmid.

Also provided in an embodiment herein is a genetically modified microbial cell for use in a biologically based test system for the detection of isothiocyanates (ITC) from samples, where the genetically modified microbial cell produces a detectable indicator in the presence of an ITC, and where the production of the detectable indicator is induced by an ITC-responsive promoter operably linked to the detectable indicator. In specific embodiments, the microbial cell is *Pseudomonas fluorescens*.

An additional embodiment provided herein is a method for detecting an isothiocyanate in a sample, comprising the steps of: 1) contacting a sample with the biologically based test system described above; 2) incubating the sample mix under conditions allowing for growth of the genetically modified microbe of the biologically based test system; 3) detecting the presence of the detectable indicator, thus detecting the presence of at least one isothiocyanate. In some embodiments, the sample is a soil sample, a plant sample, or a seed sample. In specific embodiments, the genetically modified microbe is *Pseudomonas fluorescens*. In some embodiments, the detectable indicator is a bioluminescent indicator, such as one encoded by a lux operon or an ilux operon. In some embodiments, wherein the isothiocyanate is sulforaphane, sulforaphene, metam-sodium, or allyl ITC.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

The bars depict area under the curve response to ITCs from seed meal and the line depicts a sulforaphane reference curve.

Figure 10:
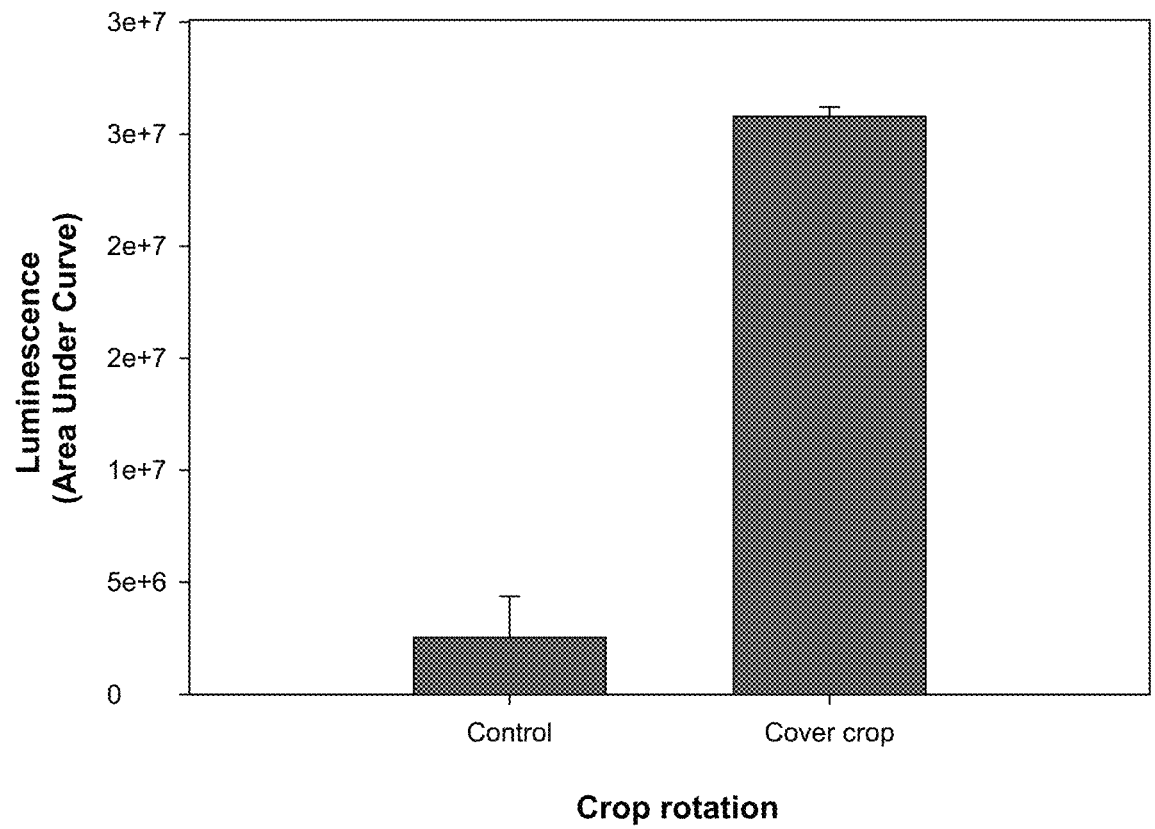

FIG. 10 provides a graphic representation of the luminescent detection of ITCs in biofumigated soil (cover cropped field soil). The cover crop was a two variety mix of *Brassica juncea* Caliente 199 and Caliente Rojo (producing allyl ITC). Area under the curve values are shown as the average and standard deviation of two assays conducted from different soil aliquots and on different days. The luminescence was provided by the ilux biosensor constructed from *P. fluorescens* SBW25 expressing an ilux operon under the control of the saxA promoter.

Figure 11:
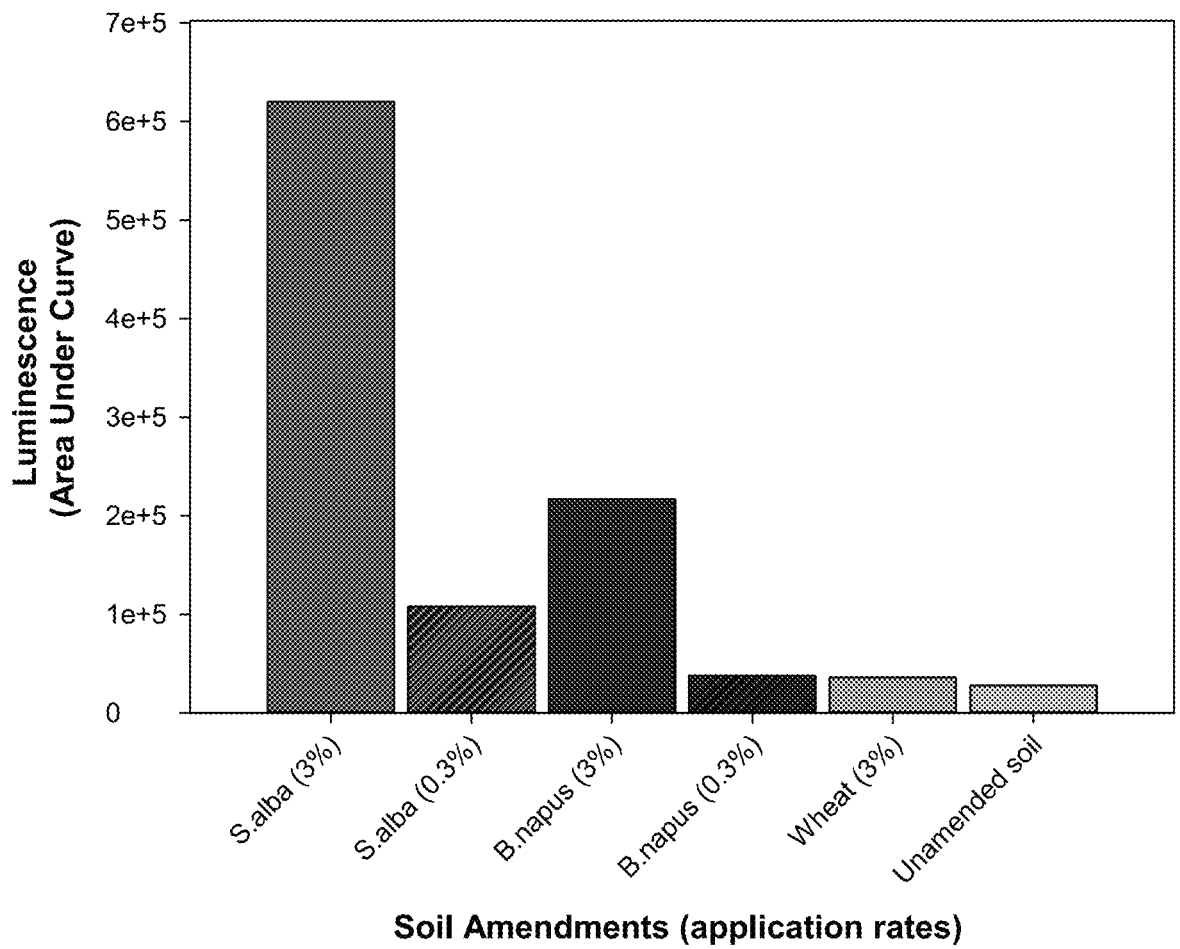

FIG. 11 provides a graphic representation of the luminescent detection of ITC in seed meal-amended soil. Soil was amended with *Brassica napus, Sinapsis alba*, or wheat straw at rates of 3% or 0.3% weight/dry weigh. The soils were incubated in gas-impermeable bags for one day. *B. napus* species produce namely 2-propenyl ITC, 3-butenyl ITC, and 4-pentenyl ITC whereas the 4-hydroxybenzyl ITC is the predominant form of *S. alba*. The luminescence was provided by the ilux biosensor constructed from *P. fluorescens* SBW25 expressing an ilux operon under the control of the saxA promoter.

DETAILED DESCRIPTION OF THE INVENTION

Isothiocyanates (ITCs) are produced in the above and belowground tissues of a variety of plants, including cruciferous plants within the Brassicaceae family. ITCs act as fumigants and are used to control plant pathogens, pests, and weeds by cover cropping with cruciferous plants or amending the soil with seed meal. However, the presence of residual ITCs in soil can inhibit seed germination and root growth and damage leaf tissues in recently planted crops. Therefore, it is important that farmers deploying plant-based fumigants know when fumigated soils are safe to plant. Unfortunately, current ITC detection techniques require complicated analyses performed in a laboratory. As such, we sought to develop a safe and easy biological sensor to detect ITCs.

The non-pathogenic bacterium *Pseudomonas fluorescens* SBW25 is resistant to ITCs. Resistance of this strain and other pseudomonads is mediated through ITC-induced production of a biochemical pathway encoded by the saxCAB operon (Fan et al., *Science*, (2011), 331(6021): 1185-1188). To construct our reporter, we linked the ITC-responsive saxA promoter to the ilux operon that produces light (Gregor et al., *Proc. Natl. Acad. Sci.*, (2018) 115(5) 962-967). The biosensor was completed by integrating the reporter into the *P. fluorescens* SBW25 genome, resulting in a bacterium producing bioluminescence upon exposure to ITCs. The biosensor is responsive to a variety of ITCs and the luminescence produced is proportional to the ITC concentration.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wisconsin, USA) using the default scoring matrix with a gap creation penalty of 50 and a gap extension penalty of 3.

The phrase "high percent identical" or "high percent identity", and grammatical variations thereof in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In an exemplary embodiment, a high percent identity exists over a region of the sequences that is at least about 16 nucleotides or amino acids in length. In another exemplary embodiment, a high percent identity exists over a region of the sequences that is at least about 50 nucleotides or amino acids in length. In still another exemplary embodiment, a high percent identity exists over a region of the sequences that is at least about 100 nucleotides or amino acids or more in length. In one exemplary embodiment, the sequences are high percent identical over the entire length of the polynucleotide or polypeptide sequences.

Having generally described this invention, the same will be better understood by reference to certain specific examples, which are included herein to further illustrate the invention and are not intended to limit the scope of the invention as defined by the claims.

Molecular Biological Methods

An isolated nucleic acid is a nucleic acid the structure of which is not identical to that of any naturally occurring nucleic acid. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

The term recombinant nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Recombinant host cells, in the present context, are those which have been genetically modified to contain an isolated nucleic molecule of the instant invention. The nucleic acid can be introduced by any means known to the art which is appropriate for the particular type of cell, including without limitation, transformation, lipofection, electroporation or any other methodology known by those skilled in the art.

In practicing some embodiments of the invention disclosed herein, it is useful to modify the genomic DNA of a strain of P. fluorescens or another target organism. In many embodiments, such modification involves deletion of all or a portion of a target gene, including but not limited to the open reading frame of the target gene, transcriptional regulators such as promoters of the target gene, and any other regulatory nucleic acid sequences positioned 5' or 3' from the open reading frame. Such deletional mutations can be achieved using any technique known to those of skill in the art. One such approach is to utilize a "deletion cassette" or "knockout cassette" (See, e.g., Fonzi and Irwin, *Genetics*, 134(3):717-28 (1993)). Knockout cassettes typically comprise at least three nucleic acid components: 1) an isolated nucleic acid that is homologous to a 5' region of a target gene or other locus; 2) an isolated nucleic acid that serves as a marker; and 3) an isolated nucleic acid that his homologous to a 3'region of a target gene or other locus. Other genetic elements can be included, depending on the particular application and design of the cassette. A knockout cassette is then introduced into an organism of interest via any appropriate means known in the art (e.g., electroporation). Taking advantage of intracellular processes such as homologous recombination, the knockout cassette integrates into the genome of the target cell. In some instances, this initial integration event deletes all or part of the target gene or locus replacing the wild type genomic DNA and deleting or "knocking out" the wild type DNA between the 5' and 3' nucleic acids of the knockout cassette. In other instances, the initial integration of the knockout cassette is followed by a subsequent recombinatorial event that results in the deletion of the target gene or locus, such as by introducing heterologous DNA flanking the gene or locus of interest and inducing homologous recombination between the two heterologous DNA segments. Knockout cassettes can be constructed in a variety of ways known in the art (e.g., split marker transformation). Knockout cassettes can contain multiple markers that allow one skilled in the art to detect initial integration events and subsequent recombinatorial events. Other methods of genomic integration known in the art, such as transposon-mediated genome, may also be used.

Where a recombinant nucleic acid is intended for expression, cloning, or replication of a particular sequence, DNA constructs prepared for introduction into a prokaryotic or eukaryotic host will typically comprise a replication system (i.e. vector) recognized by the host, including the intended DNA fragment encoding the desired polypeptide, and can also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

In some instances, a host cell other than *P. fluorescens* can serve as a recipient for recombinant DNA. For example, a bacterial host may be utilized to clone a plasmid in which a deletion cassette is constructed, replicated, or analyzed. In such instances, a recombinant DNA fragment may require an appropriate promoter and other necessary vector sequences that can be readily selected so as to be functional in the host. Examples of workable combinations of cell lines and expression vectors are described in Sambrook et al. (1989) vide infra; Ausubel et al. (Eds.) (1995) *Current Protocols in Molecular Biology*, Greene Publishing and Wiley Interscience, New York; and Metzger et al. (1988) *Nature*, 334: 31-36. Many useful vectors for expression in bacteria, yeast, fungal, mammalian, insect, plant or other cells are well known in the art and may be obtained from commercial vendors or constructed de novo.

Knockout cassettes, vectors and other nucleic acids introduced into a host cell will likely contain a selectable marker, that is, a gene encoding a protein necessary for the survival or growth of a host cell transformed with the nucleic acid. Although such a marker gene may be carried on another polynucleotide sequence co-introduced into the host cell, it is most often contained on the transforming nucleic acid. Only those host cells into which the marker gene has been introduced will survive and/or grow under selective conditions. Typical selection genes encode proteins that (a) confer resistance to antibiotics or other toxic substances, e.g., hygromycin, ampicillin, neomycin, methotrexate, etc.; (b) complement auxotrophic deficiencies; or (c) supply critical nutrients not available from complex media. The choice of the proper selectable marker will depend on the host cell and appropriate markers for different hosts are well known in the art.

Selectable markers useful in practicing the methodologies of the invention disclosed herein can be "positive selectable markers". Typically, positive selection refers to the case in which a genetically altered cell can survive in the presence of a toxic substance only if the recombinant polynucleotide of interest is present within the cell. For example, when a recombinant deletion cassette introduced into a cell contains a hygromycin B resistance gene, only those transformants containing the recombinant polynucleotide will survive when grown in the presence of hygromycin B. Other positive markers include, but are not limited to, mutated beta-tubulin (ben) gene, which confers resistance to benomyl; Bar, which confers resistance to phosphinothricin; Ble, which confers resistance to phleomycin; Sat-1, which confers resistance to nourseothricin, amp, which confers resistance to ampicillian; Kan, which confers resistance to kanamycin; and cbx, conferring resistance to carboxin. Genes essential for the synthesis of an essential nutrient (such as amino acid arginine and nucleoside pyrimidine) may also be used as positive selection markers and are contemplated by the present invention. Negative selectable markers and screenable markers are also well known in the art and are contemplated by the present invention.

Screening and molecular analysis of genetically altered strains, as well as creation of desired isolated nucleic acids can be performed using any methodology known in the art, including, but not limited to, Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) *Science* 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquati-* cus, the amplification process can be completely automated. Other enzymes which can be used are known to those skilled in the art.

Biosensor Host Cells

Host cells utilizable in the present disclosure are microbes that are capable of expressing recombinant genes allowing for the production of bioluminescence in the presence of ITCs. At a minimum such recombinant genes include an ITC-responsive element (e.g., a promoter) in operable conjunction with a detectable indicator, such as bioluminescence (e.g., the ilux operon). Those skilled in the art will recognize that these components can be integrated into the host cell genome or be present on one or more integrating or non-integrating plasmids. An exemplary bioluminescence operon that can be used in practicing the present disclosure is a synthetic ilux operon originated from *Photorhabdus luminescens*, that encodes both luciferase and an enzyme complex that produces the substrate for luciferase (Gregor et al, *Proc. Natl. Acad. Sci*, (2018) 115(3): 962-967). However, any luxCDABE operon known in the art can be utilized. Other detectable indicators include other optical indicators (producing visible colorimetric, fluorometric, or light-based changes) as well as amperometric, immuno-, or gas-based indicators. For example, the fluorometric red fluorescent protein or colorimetric β-galactosidase reporters could be employed.

Any ITC-responsive promoter known in the art, or discovered in the future, may be incorporated into the modified microbes of the present disclosure. In some instances, the ITC-responsive promoter can be native to the genome of the host cell. The saxA gene encodes an isothiocyanate hydrolase, which hydrolyzes ITCs to carbonyl sulfide and amines (Welte et al, Appl. Environ. Microbiol., (2016) 82:2372-79). Identified in a wide variety of plant- and insect-associated bacteria, five phylogenetically distinct clusters have been described (van den Bosch, et al, Appl. Environ. Microbiol., (2018) 84). SaxA proteins from different phylogenetic clusters are non-specific to ITC side chains, and, due to the non-specificity of these enzymes, we expect most of the promoters for the various genes encoding these proteins to respond to most ITCs side chains. As such, although a single saxA promoter (SEQ ID NO: 1) is utilized in the Examples, the present disclosure includes the expectation that most promoters of saxA, saxA homologs, and other genes specifically-induced by ITC will function as the ITC-responsive element for a biosensor of the present invention.

In addition to bioluminescent detectable indicators such as the luxCDABE operon, ilux operon, and modified versions of these, other luminescent or fluorescent indicators known in the art can be utilized (e.g., green fluorescent protein, enhanced green fluorescent protein, yellow fluorescent protein, enhanced yellow fluorescent protein, etc). In some embodiments of the present disclosure, the host cell is resistant to ITC-induced death or growth inhibition.

Host cells that can be utilized as a biosensor can include any microbe (bacteria, fungi, alga, protist) or single cell (e.g., animal cell line) transformable with the biosensor detection machinery (e.g., an ITC responsive regulatory element, such as a promoter, operably combined with a indicator gene or detector operon, such as luxCDABE or ilux). A preferred host cell will have native or engineered resistance to ITCs. Alternative hosts include, but are not limited to other *Pseudomonas* spp. like *P. cannabina* and *P. syringae*, *Pectobacterium* spp., as well as eukaryotic hosts like *Pichia pastoris* and *Saccharomyces* spp.

Host cells that can be utilized as a biosensor can include any microbe (bacteria, fungi, alga, protist) or single cell (e.g., animal cell line) transformable with the biosensor detection machinery (e.g., an ITC responsive regulatory element, such as a promoter, operably combined with a detector operon, such as luxCDABE or ilux). A preferred host cell will be ITC-resistant.

Culture Conditions for Biosensor Growth and ITC Detection

One of skill in the art will recognize that multiple culture conditions can be modified in practicing the present disclosure. One of skill in the art will recognize that culture parameters affecting a particular microbial species that serves as a biosensor of the present disclosure can be varied to suit that organism to achieve optimal growth parameters. For example, a biosensor comprising a *P. fluorescens* strain expressing an ilux operon under control of a saxA promoter, would have different basal nutritional requirements from a yeast species (e.g., *S. cerevisiae*) expressing a codon-optimized ilux operon under control of an ITC-responsive promoter.

Common, but non-limiting culture parameters include temperature, pH, oxygen availability, and nutrient base. For example, a biosensor culture can be grown at a temperature of 15° -37° C., or any whole or partial degree within that range, including, but not limited to 15.0° C., 15.5° C., 16.0° C., 16.5° C., 17.0° C., 17.5° C., 18.0° C., 18.5° C., 19.0° C., 19.5° C., 20.0° C., 20.5° C., 21.0° C., 21.5° C., 22.0° C., 22.5° C., 23.0° C., 23.5° C., 24.0° C., 24.5° C., 25.0° C., 25.5° C., 26.0° C., 26.5° C., 27.0° C., 27.5° C., 28.0° C., 28.5° C., 29.0° C., 29.5° C., 30.0° C., 30.5° C., 31.0° C., 31.5° C., 32.0° C., 32.5° C., 33.0° C., 33.5° C., 34.0° C., 34.5° C., 35.0° C., 35.5° C., 36.0° C., 36.5° C., and 37.0° C. Additionally, biosensor cultures can be grown in media where the pH is between 5.5 and 8.5, 6.0 and 7.5, or any value within that range, including, but not limited to pH 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5. One of skill in the art will recognize that a stable pH does not need to be maintained throughout the entirety of the growth of the strain, thus, in some embodiments, the pH of a microbial culture of the present invention will vary over time. In other embodiments, pH buffers can be added to maintain a relatively stable pH where the pH of the culture medium over the life of the culture does not vary from a chosen starting point by more than ±0.5. Nutritional parameters can also be varied, including nitrogen sources, carbon sources, phosphate sources, trace elements, vitamins, and minerals. Each of these is known to the skilled artisan and can readily be adjusted to suit the specific biosensor utilized.

Isothiocyanates

Isothiocyanates (ITCs) are compounds naturally produced by several plants belonging to the families Brassicaceae, Capparaceae and Caricaceae as a system of defense against pathogen attack and produced by the hydrolysis of glucosinolates by the enzyme myrosinase. There are at least 132 glucosinolates in nature (Agerbirk and Olsen, *Phytochem.*, (2012), 77:16-45) with potential to produce as many cognate ITCs. The present disclosure encompasses detection of such naturally occurring ITCs, as well as synthetic ITCs and synthetic analogs. Commonly used ITCs and plants in biofumigation include allyl ITC (black/brown mustard), p-hydroxybenzyl ITC (white mustard), and 4-pentenyl ITC (turnip, rapeseed) (Kirkegaard and Sarwar, Plant and Soil, (1998) 201: 71-89).

EXAMPLES

Example 1

Luminescence Reporter Plasmid (Biosensor) Validation

The plasmid vector pUC18T-Tn7T-lux-Gm (Damron et al., Appl. Environ. Microbiol. (2013) 79(13): 4149-4153), which contains Tn7 sites for integration into the *P. fluorescens* genome, a luxCDABE operon responsible for bioluminescence, and a gentamicin resistance marker. This plasmid also contained a p1 promoter, an unregulated promoter upstream of the luxCDABE operon, which was removed and replaced with the desired promoter.

The saxA promoter was PCR amplified from *Pseudomonas cannabina* and cloned upstream of the luxCDABE gene operon. Proper insertion was confirmed by sequencing and with gel electrophoresis prior to transformation of a highly competent *E. coli* host strain. The resulting plasmid containing the luxCDABE operon under control of the saxA promoter was termed pHT #3. This plasmid was transformed into *P. fluorescens* SBW25, via electroporation and selected for gentamicin resistance. The genomic DNA was extracted and sequenced to confirm proper integration.

*P. fluorescens* SBW25 transformed with pHT #3 (saxA promoter functionally fused with the luxCDABE operon) was tested for functionality in a basic microplate assay with the sulforaphane, the predominant ITC in broccoli, at concentrations ranging from 0-100 μM. For the basic microplate assay, the reporter biosensor was cultivated overnight in LB media with 50 μg/mL carbenicillin and 15 μg/mL gentamicin. The 200 μL assay was performed in opaque 96-well microtiter plates by adding ITC sample to the reporter cells at a final concentration of 0.05 OD600 in LB medium. All assay plates included cell-only controls (no ITC sample). Luminescence was measured in either a microplate spectrophotometer (Biotek Synergy HT) or a designated luminometer (Molecular Devices Spectramax L) for a 20-hour period in 15-minute intervals with ~500 RPM shaking. Data were collected using auto-scaled gain or photon counting to increase signal detection. Modifications to the assay for the luxCDABE-based biosensor included a lower bacterial OD600 of 0.005, incubation at 31° C., and measurement every 30 min.

Figure 1A:
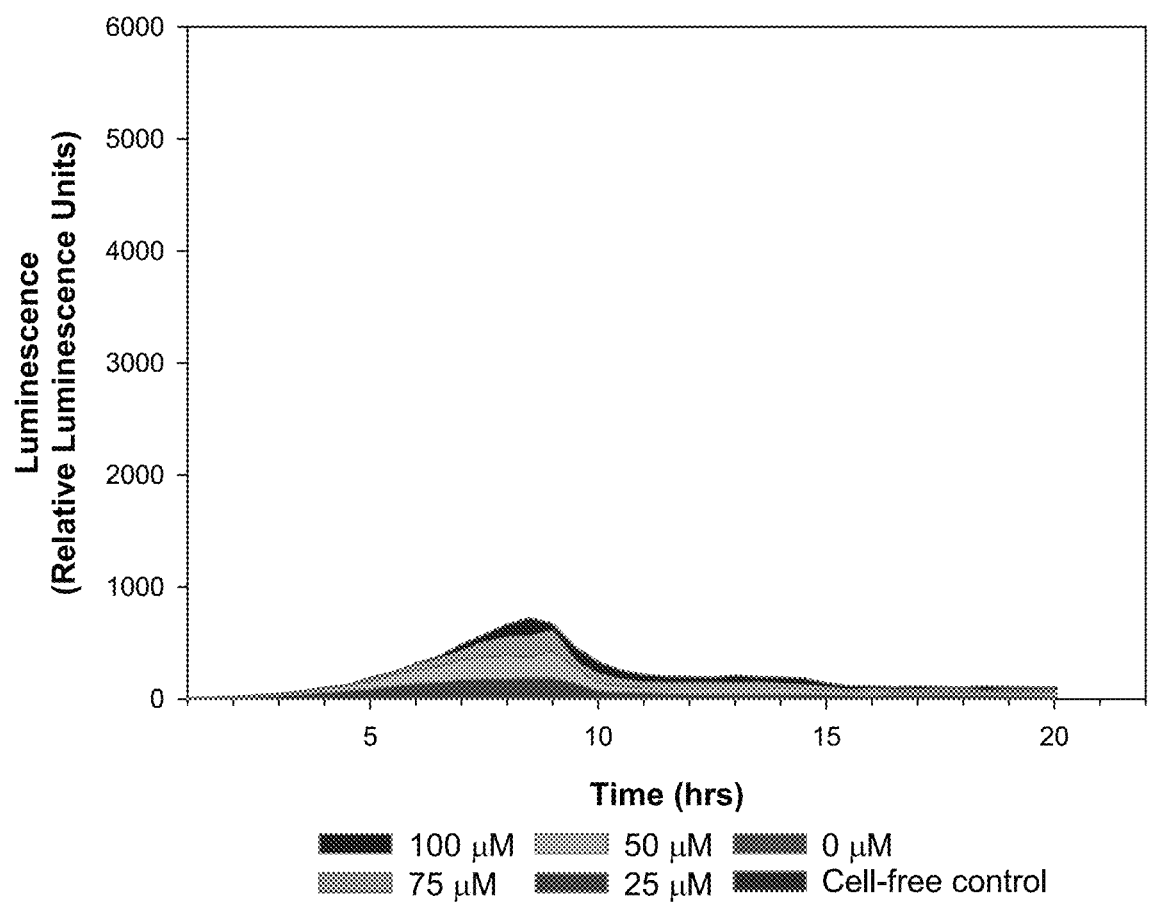
FIG. 1A and FIG. 1B provide graphic representation of the luminescence of *P. fluorescens* SBW25 expressing the luxCDABE operon under control of the saxA promoter (luxCDABE biosensor) in response to varying sulforaphane concentrations (0, 25, 50, 75, 100 μM). Luminescence is shown as relative luminescence units (RLU) in FIG. 1A and as the definite integral of the luminescence curve (area under the curve) in FIG. 1B.
Figure 1B:
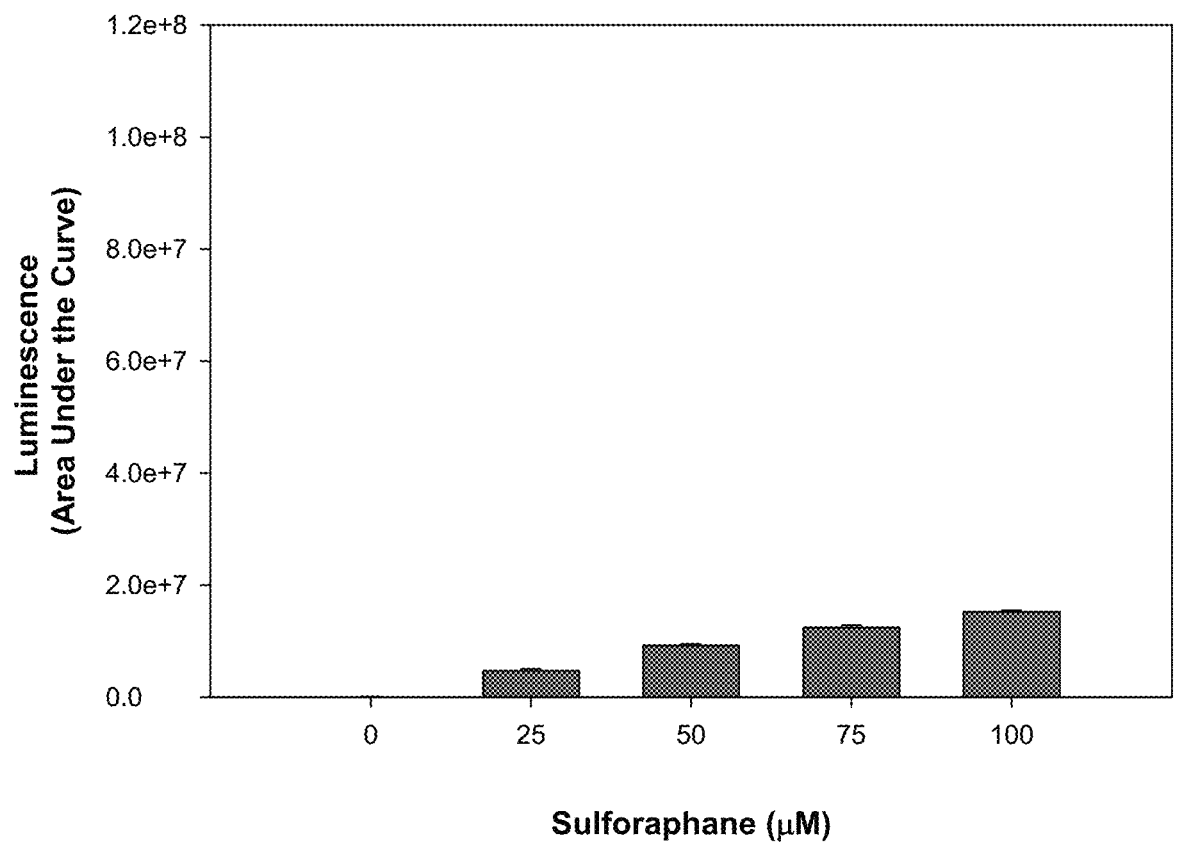

As shown in FIG. 1A and FIG. 1B, the *P. fluorescens* SBW25 strain expressing the luxCDABE operon under control of the saxA promoter exhibited a peak luminescence approximately 8-9 hours after inoculation regardless of the concentration of ITCs present in the solution. This biosensor exhibited almost no background luminescence in the absence of sulforaphane. The peak luminescence measured for 100 μM of ITC was at approximately 700 relative light units (RLUs) or an area under the curve (AUC) value of $1.5 \times 10^7$. The biosensor showed a dose dependent response to the amount of ITC present in the sample.

To increase the luminescent signal, the luxCDABE operon of the pHT #3 plasmid was replaced with the enhanced ilux operon that has an additional open reading frame encoding flavin mononucleotide (FMN) reductase and other optimizations (Gregor et al, *Proc. Natl. Acad. Sci.*, (2018) 115(3): 962-967). All other components remained the same as the precursor, and this plasmid was assembled using the Gibson Assembly method (Gibson et al, *Nature Meth.*, (2009) 6(5):343-347). The resulting plasmid, named pHT #9, was integrated into the *P. fluorescens* SBW25 genome in the same manner as pHT #3. Integration into the genome was confirmed by PCR and the reporter was validated using the basic microplate assay described above.

Figure 2A:
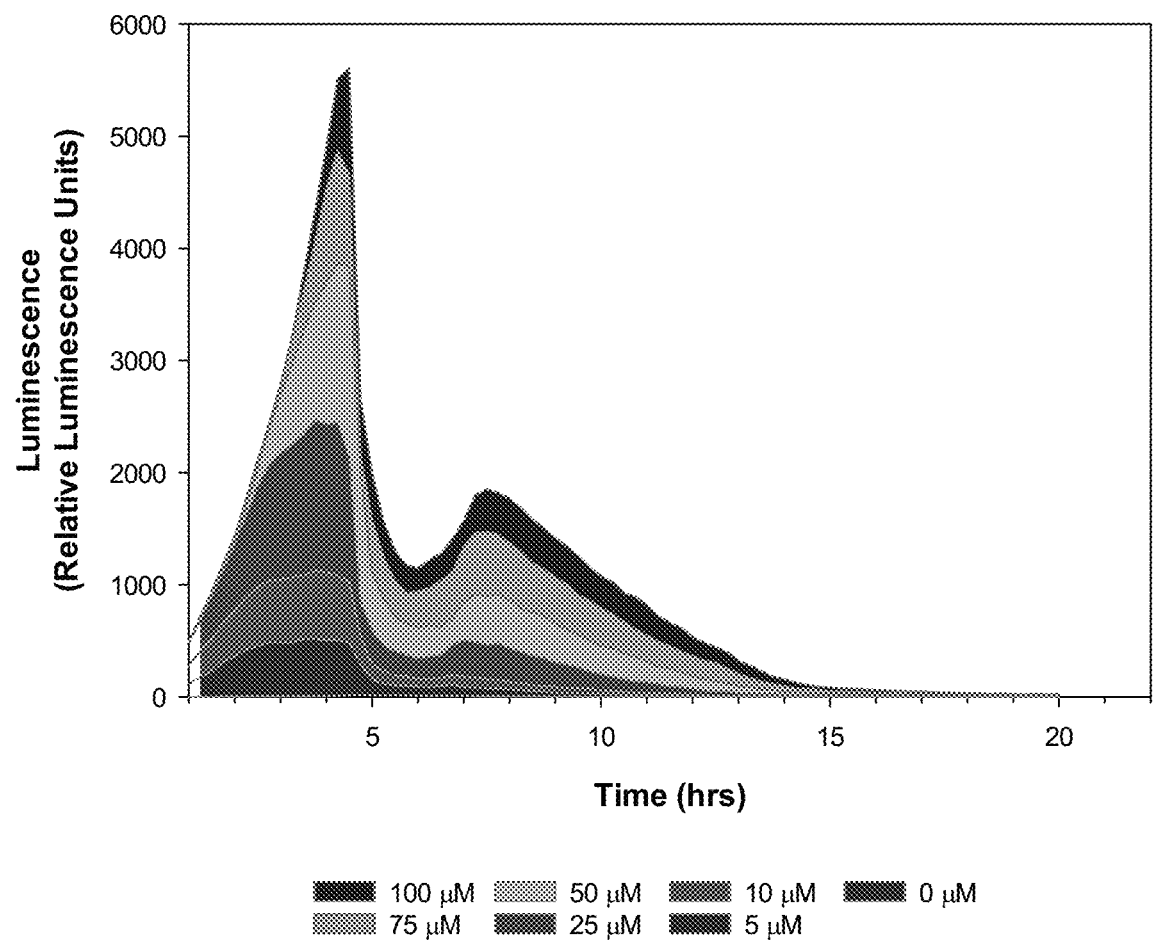
FIG. 2A and FIG. 2B provides a graphic representation of the luminescence of *P. fluorescens* SBW25 expressing an ilux operon under control of the saxA promoter (ilux biosensor) in response to varying sulforaphane concentrations (0, 5, 10, 25, 50, 75, 100 µM). Luminescence is shown as relative luminescence units (RLU) in FIG. 2A and as the definite integral of the luminescence curve (area under the curve) in FIG. 2B.
Figure 2B:
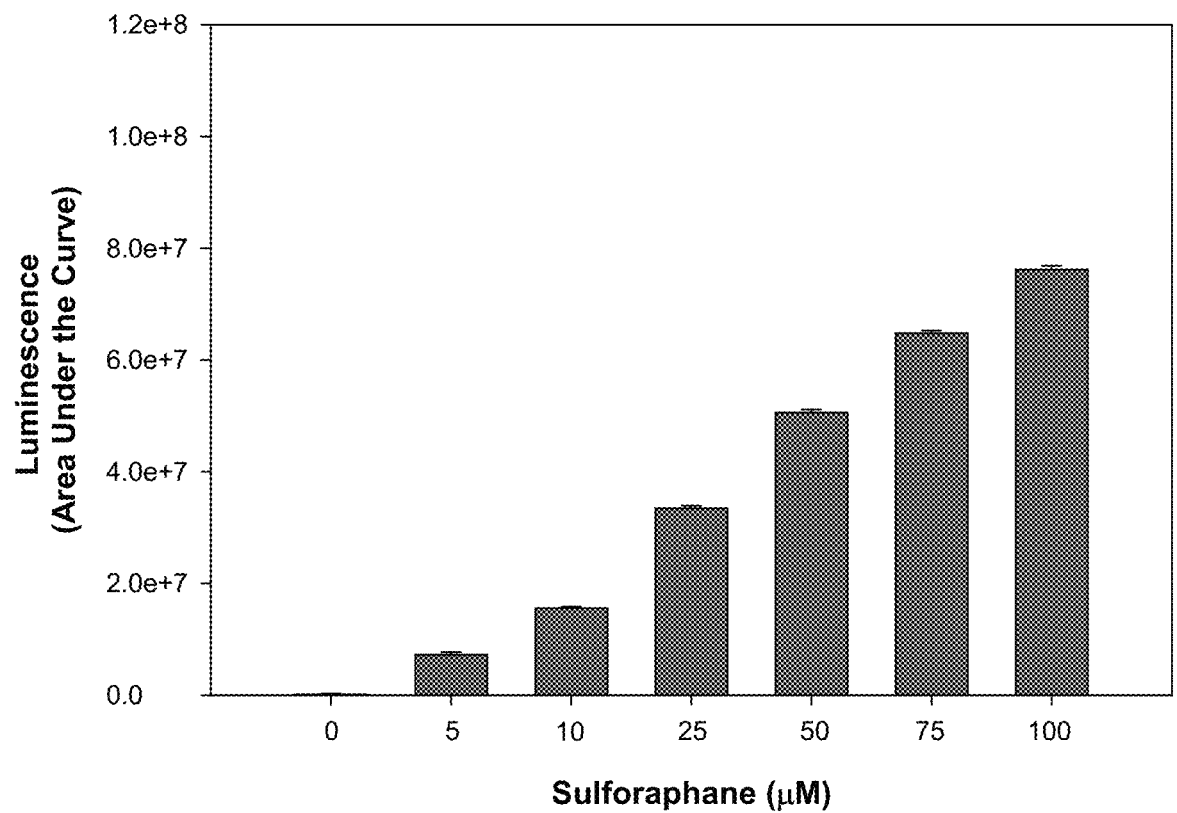

As shown in FIG. 2A and FIG. 2B, *P. fluorescens* SBW25 expressing an ilux operon under control of a saxA promoter showed a dose-dependent response to the amount of ITC present in the growth medium. Compared to the luxCDABE biosensor, the ilux biosensor had a more rapid (initial peak around 4-4.5 hours) and a stronger response to sulforaphane as demonstrated with the 100 μM dose by a 2-fold increase in AUC and 7.7-fold increase in the maximum RLU.

Figure 3:
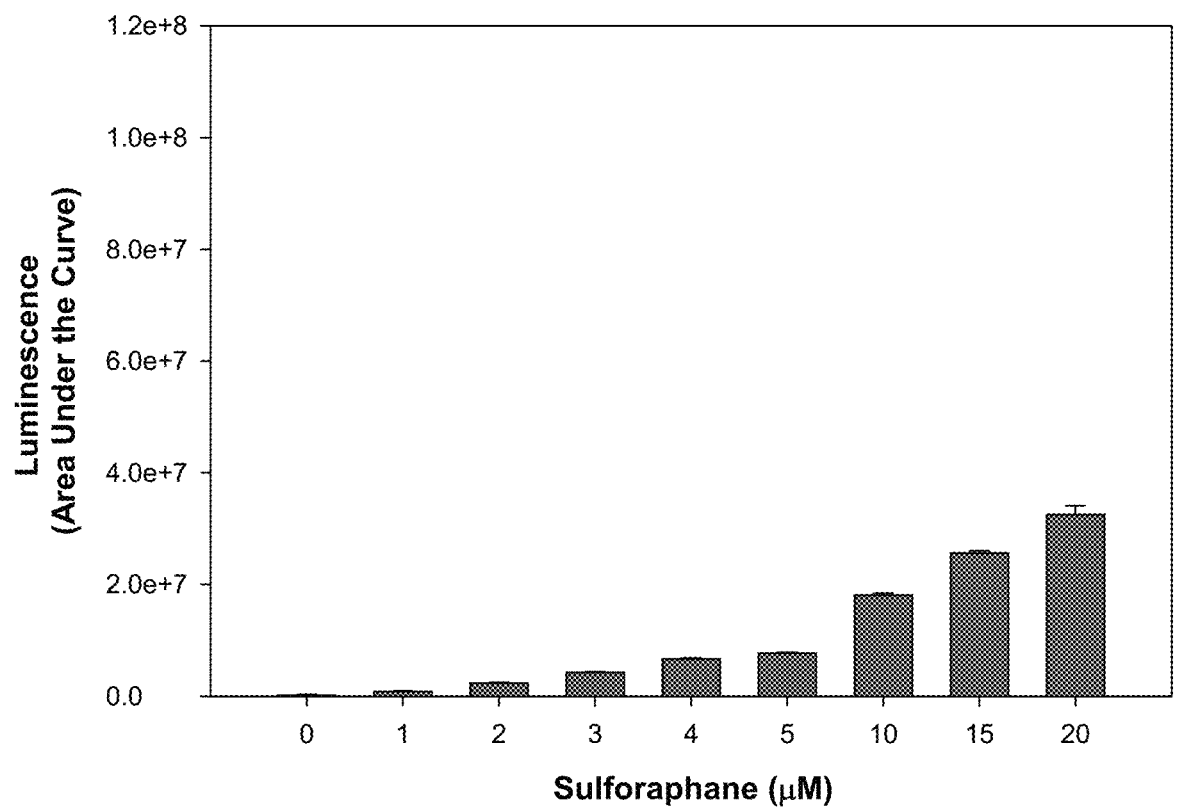
FIG. 3 provides a graphic representation of the luminescence of *P. fluorescens* SBW25 expressing an ilux operon under control of the saxA promoter (ilux biosensor) in response to low-dose sulforaphane concentrations (0-20 µM).

Given the increased response of the ilux biosensor, the limits of detection were tested in a lower range of sulforaphane to a 1 μM concentration. The results shown in FIG. 3 demonstrate that the *P. fluorescens* SBW25 biosensor with the ilux operon was able to detect sulforaphane at concentrations of 1-2 μM.

Example 2

Biosensor Detection of Different ITCs

Figure 4:
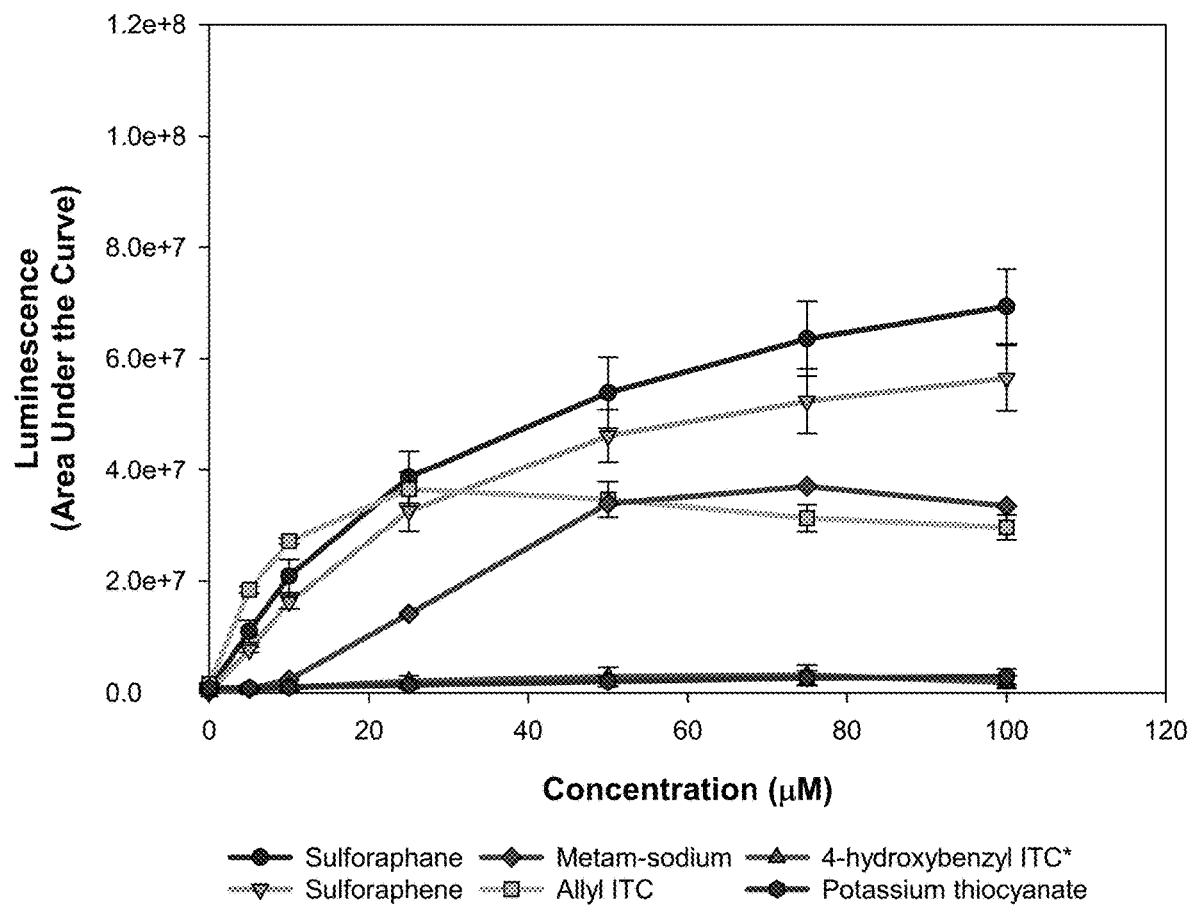
FIG. 4 provides a graphic representation of the luminescent detection of different ITCs by the ilux biosensor constructed from *P. fluorescens* SBW25 expressing an ilux operon under the control of the saxA promoter (SEQ ID NO: 1). Area under the curve values are shown as the mean and standard error for different experiments (n=5, sulforaphane; n=3, KSCN; n=2 sulforaphene, allyl ITC, 4-hydroxybenzyl ITC; and n=1, metam-sodium). Sulforaphane, sulforaphene, allyl ITC, and 4-hydroxybenzyl ITC are aliphatic ITCs. The synthetic pesticide metam-sodium generates an aliphatic ITC (methyl ITC). The aromatic 4-hydroxybenzyl ITC is highly unstable in aqueous solutions and forms ionic thiocyanate. Potassium thiocyanate is also an ionic thiocyanate.

The basic microplate reporter protocol was performed as detailed above. The biosensor was responsive to the aliphatic ITCs sulforaphane, sulforaphene, and synthetic methyl ITC (Metam-sodium), but not 4-hydroxybenzyl ITC (FIG. 4). The inability to detect 4-hydroxybenzyl ITC is likely due to the highly unstable nature of this ITC in aqueous solutions with a half-life of 6 min at pH 6 (Borek and Morra, *J. Agric. Food Chem.*, (2005) 53:8650-54). The major product of 4-hydroxybenzyl degradation is ionic thiocyanate (SCN⁻) at neutral pH and the biosensor did not respond to either 4-hydroxybenzyl ITC (presumably SCN⁻) or potassium thiocyanate (also ionic thiocyanate). However, these results show that the biosensor is responsive to multiple ITCs.

Example 3

Analysis of ITCs from Plant Extracts and Seed Meal

To determine whether the ilux biosensor system could detect plant-derived ITC and distinguish between ITC-forming and non-ITC-forming plants we tested extracts prepared from germinated seeds of ITC-forming daikon, broccoli, radish, kale, mustard, and arugula and non-ITC-forming mung bean, alfalfa, clover. The predominant ITC formed by broccoli is sulphoraphane. Daikon produces two main ITCs, 4-(Methylthio)-3-butenyl isothiocyanate and a lesser amount of phenethyl isothiocyanate (Nakamura et. al, *J. Agric. Food Chem.*, (2001) 49(12):5755-5760). Kale produces sulphoraphane, phenylethyl ITC, and allyl ITC (Kim et al., *Sci. Reports*, (2018) 8(1):1-11). Arugula produces the ITC erucin, and mustard produces allyl isothiocyanate. The primary ITCs of radish are sulforaphane and raphasatin (Hanlon and Barnes, *J. Food Sci.*, (2011) 76(1): C185-192).

Plant extracts were prepared from seeds germinated in small petri dishes containing 0.5×Murashige and Skoog Medium and 0.3% agar for up to 4-days under artificial lighting. Germinated seeds and/or seedlings were transferred to 2-mL screwcap tubes containing steel beads. Water was added at a 1:2 ratio of plant weight to water volume. The tissue was macerated and pelleted by centrifugation. Supernatants were diluted prior to use in the basic microplate protocol. Different germination times were assessed with broccoli and daikon to determine when the plants exhibited the greatest ITC concentrations.

Figure 5:
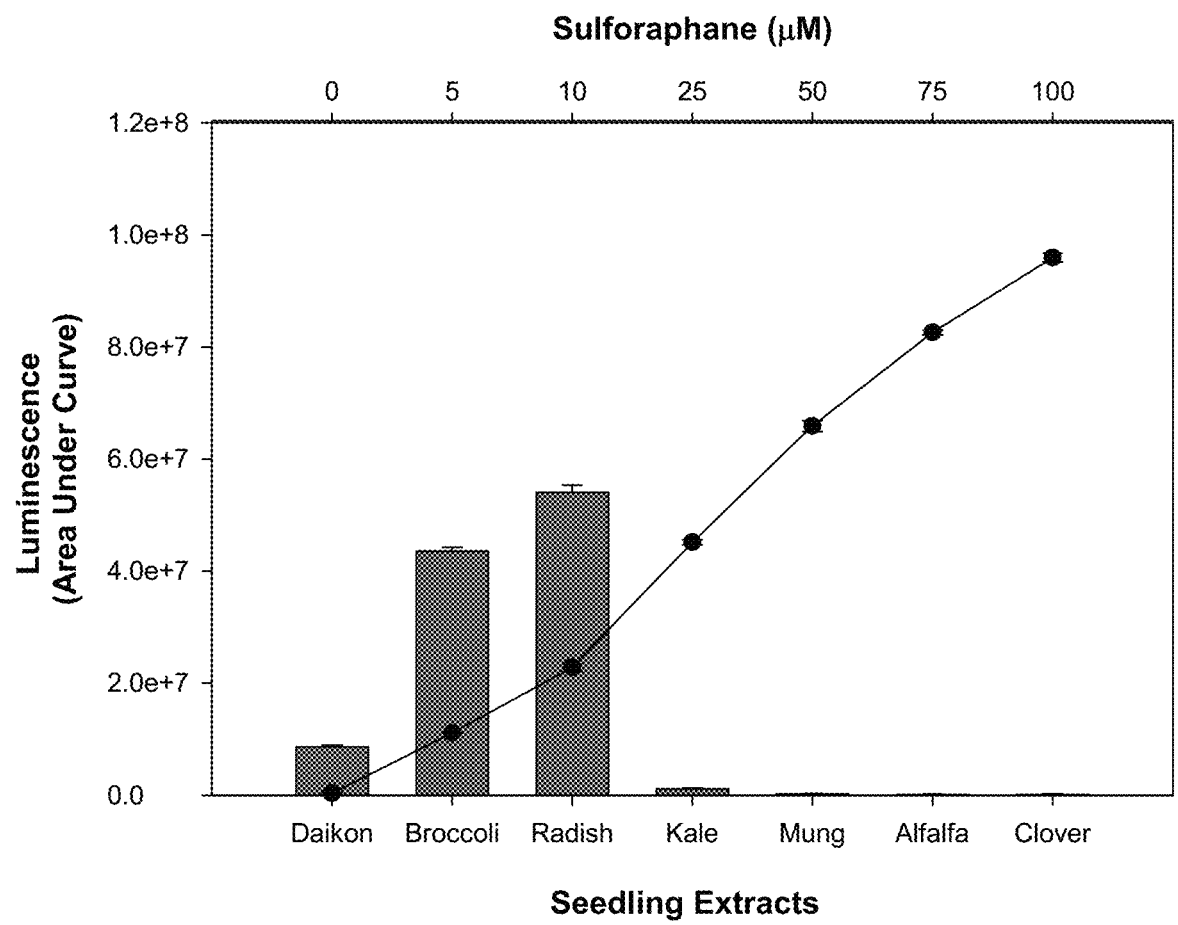
FIG. 5 provides a graphic representation of luminescence produced by the *P. fluorescens* SBW25 expressing an ilux operon under the control of the saxA promoter (dux biosensor) in extracts with ITC-producing (daikon, broccoli, radish, kale) and non-ITC-producing plants (mung bean, alfalfa, clover). The bars depict area under the curve response to ITCs from seedlings and the line depicts a sulforaphane reference curve.

As shown in FIG. 5, luminescence was detected in extracts of plants known to produce ITCs (daikon, broccoli, radish and kale). Extracts from non-ITC-producing plants (mung bean, alfalfa and clover) did not produce levels of luminescence above the background (0 µM sulforaphane). The low amount of luminescence produced by kale extract may either be due to plant-based effects (e.g. low ITC) or inhibition which has been observed in experiments and can be ameliorated by dilution of the plant extracts (data now shown).

Figure 6:
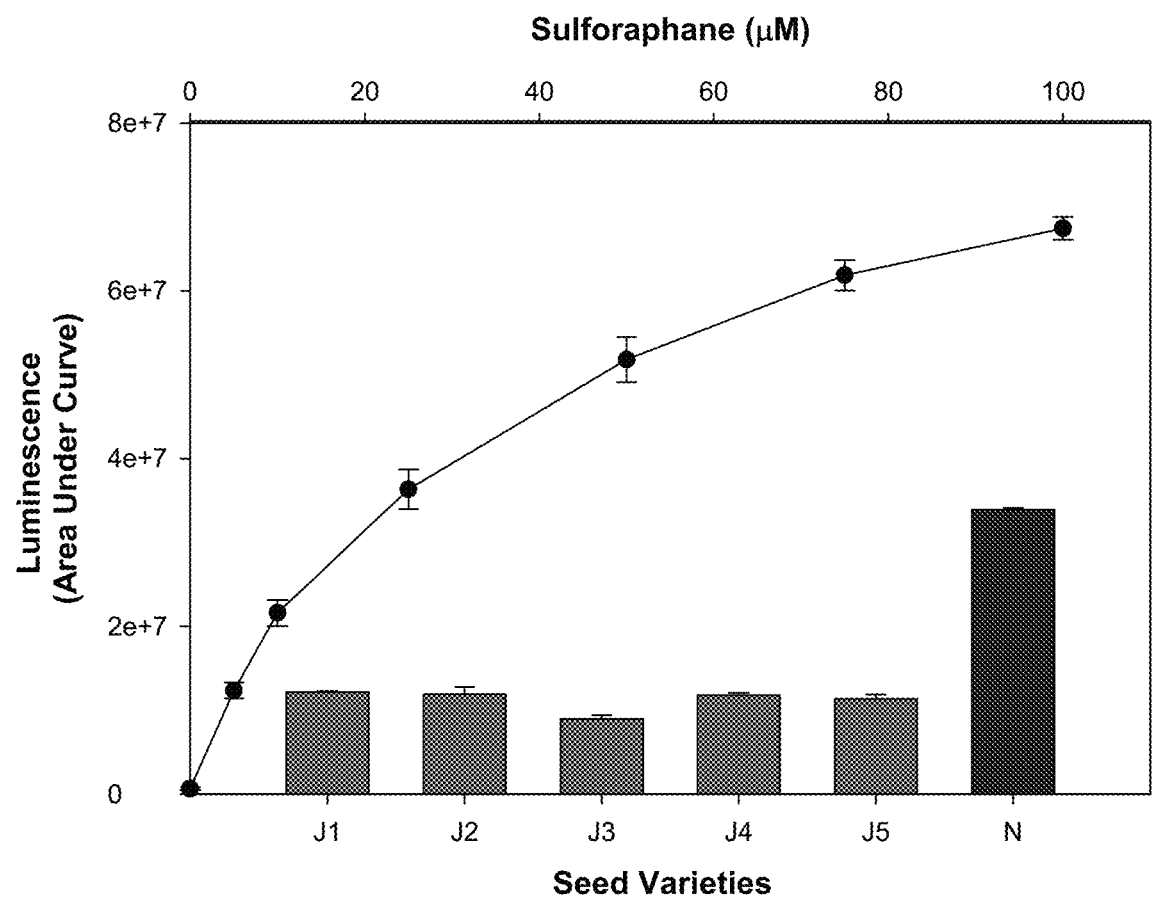
FIG. 6 provides a graphic representation of luminescent detection of different ITCs generated by different seedlings. Area under the curve values are shown as the mean and standard error of two different experiments. Seed varieties J1-J5 are mustard (producing allyl ITC) and variety N is arugula (producing erucin). The luminescence was provided by the ilux biosensor constructed from *P. fluorescens* SBW25 expressing an ilux operon under the control of the saxA promoter. The bars depict area under the curve response to ITCs from seedlings and the line depicts a sulforaphane reference curve.

As shown in FIG. 6, luminescence was detected in germinated seeds of B. juncea and arugula. The luminescence was relatively similar between the different lots of B. juncea seed compared to the arugula which produced an AUC of nearly twice that of the B. juncea. This demonstrates that the biosensor can detect different ITCs from different plants.

Figure 7:
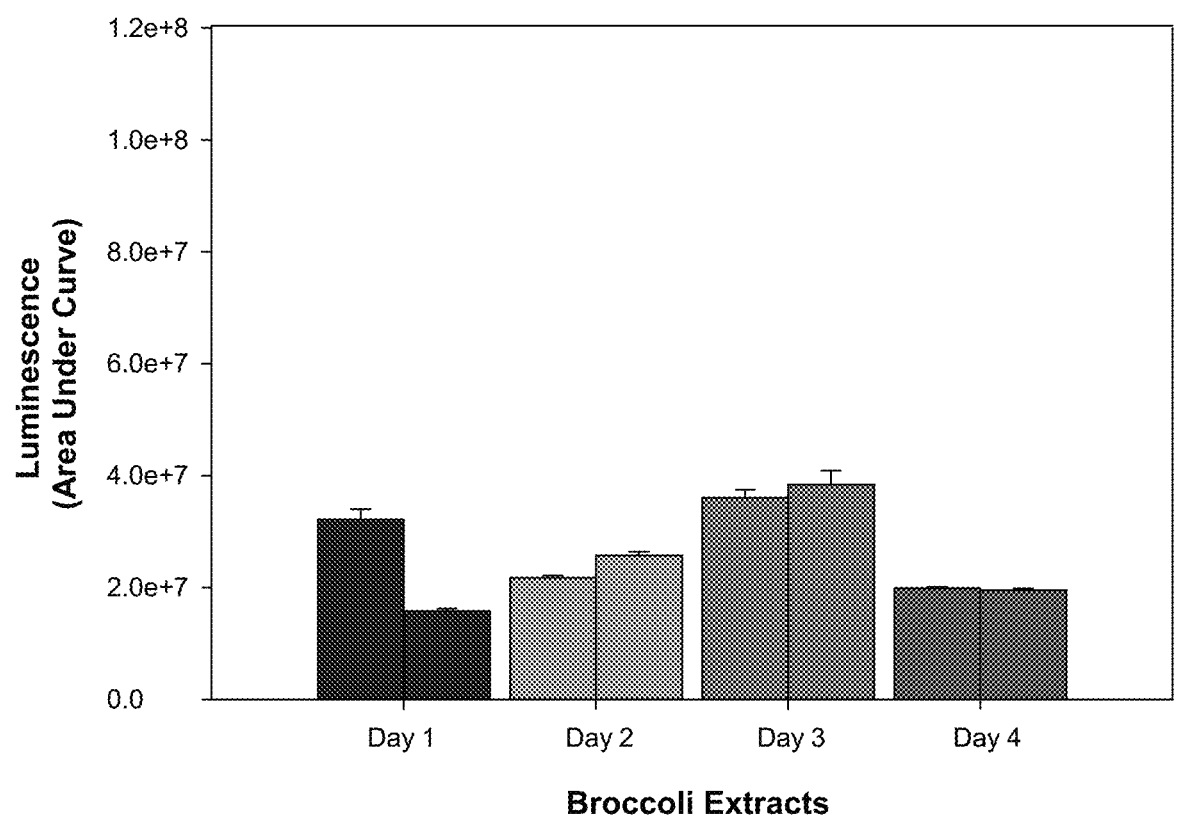
FIG. 7 provides a graphic representation of luminescent detection of changes in ITCs produced by broccoli seeds 1-4 days post germination. The luminescence was provided by the ilux biosensor constructed from *P. fluorescens* SBW25 expressing an ilux operon under the control of the saxA promoter.
Figure 8:
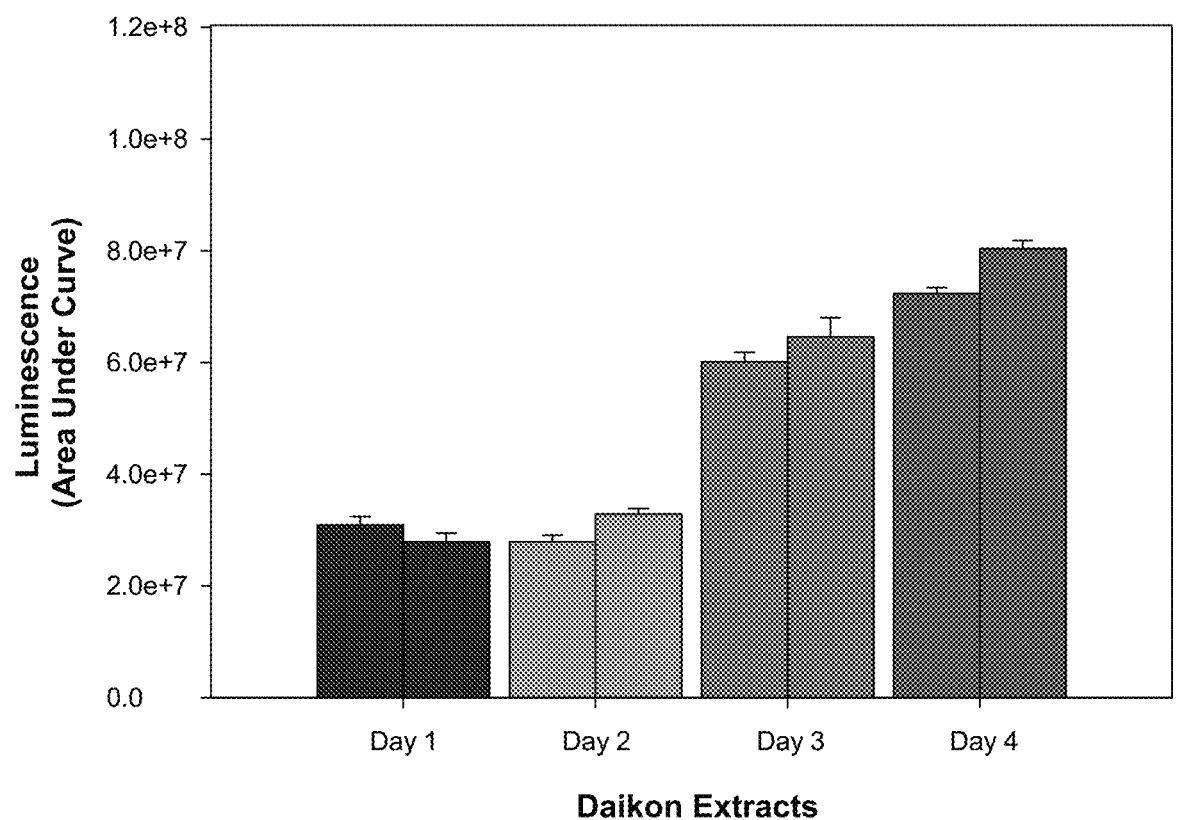
FIG. 8 provides a graphic representation of luminescent detection of changes in ITCs produced by daikon seedlings 1-4 days post germination. The luminescence was provided by the ilux biosensor constructed from *P. fluorescens* SBW25 expressing an ilux operon under the control of the saxA promoter.

As shown in FIG. 7, the biosensor detected increasing amounts of ITC up to 3 days post-germination of broccoli seeds, but the amount detected decreased on the fourth day post-germation as biomass increased. In contrast, the amount of ITC detected in daikon extracts increased across the four-day post germination period (FIG. 8).

To analyze the ability of the biosensor to detect ITCs in plant residues, seed meal was incubated on a rotating shaker at room temperature for 24 hrs with a 1:10 seed meal:water ratio (by mass) in 2.0 mL microcentrifuge tubes. Centrifuging and assaying of supernatant were conducted as described above for seedlings. Two seed meal types were tested—Sinapis alba (white mustard) and Brassica juncea (Indian mustard)—both of which are used in commercial biofumigation.

Figure 9:
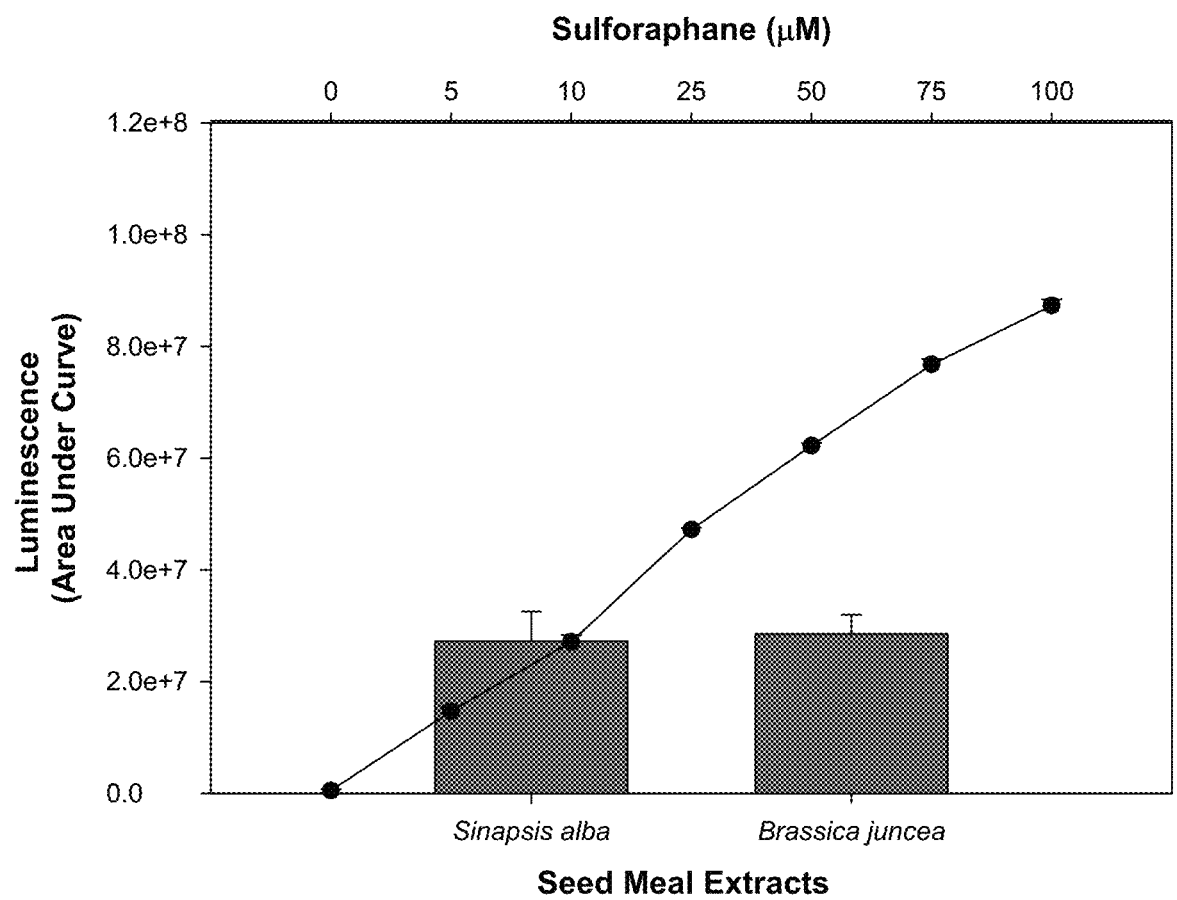
FIG. 9 provides a graphic representation of luminescent detection of ITCs in seed meal from *Brassica juncea* and *Sinapsis alba*. The luminescence was provided by the ilux biosensor constructed from *P. fluorescens* SBW25 expressing an ilux operon under the control of the saxA promoter.

The results shown in FIG. 9 demonstrate that the biosensor is effective at detecting ITCs in seed meal. Results shown are from samples after 24 hours of incubation in water. Extracts were measured as described above. Analysis showed that these two varieties of seed meal contained approximately the same quantity of detectable ITC, with comparable luminescence as the 10 µM sulforaphane reference.

Example 4

Detection of ITCs in Biofumigated and Seed Meal-Amended Soils

One predicted use of the disclosed biosensors is to test for ITC levels in treated soils, thus, we tested both biofumigated and seed meal amended soils. Biofumigated soil was collected from a field study in Hermiston, Oregon. The soils were managed in a 3-yr rotation with a Brassica cover crop mix (B. juncea Caliente 199 and Caliente Rojo; allyl ITC). The Brassica cover crop was tilled into the soil the day prior to sampling and the soils were stored frozen until analysis. Intact plant material was still visible in the frozen samples. Frozen soils were thawed and subsamples were homogenized (1600 MiniG homogenizer, 1500 RPM, 7 min), and rotated at room temperature for 45 min to allow time for glucosinolate hydrolysis. The sample was centrifuged for 5 min at 4,000×g and 100 µL extract was used in the basic microplate assay.

The ilux biosensor detected ITC in the cover cropped soil as evidenced by the greater luminescence value compared to the control soil (FIG. 10). The biosensor also detected ITC after cover cropping in a 2-yr crop rotation included in the field trial, albeit the difference between the cover cropped soil and control was marginal (data now shown). The control soils had less luminescence than the cell-only (no-ITC) control which highlights the importance of using similar extract matrices for comparisons.

For analysis of seed meal amended soil, B. napus and S. alba seed meals were each added to a moist silt loam soils at 0.3% and 3% weight/dry weight. The soil/seed meals were mixed, transferred to small zippered bags and stored in gas-impermeable bags at room temperature. Soil amended with wheat straw and unamended soil were included as ITC-free controls. Seed meal-amended or unamended soil (2 g) was transferred to a 5-mL microcentrifuge tube containing 2 mL of $H_2O$. The soil was homogenized with a probe homogenizer (VWR 250 Homogenizer) for 20 sec on the lowest setting and incubated at room temperature for 45 min to allow for hydrolysis of the plant glucosinolates. The slurry was transferred to a 2 mL tube and centrifuged for 10 min at 13,000×g to pellet the soil and native soil microbes. The supernatant (100 µL) was used directly in the basic microplate assay with the ilux biosensor.

The ilux biosensor detected ITCs in both S. alba and B. napus seed meal-amended soil at 3% amendment rate (FIG. 11). When added at 0.3% rate, ITC was detected in only the S. alba seed meal. The ITCs in the soil amended with 0.3% B. napus were below detection based on the comparison of the luminescence values with the wheat-amended and unamended soil controls. Sulforaphane is the predominant ITC of S. alba and B. napus species produce 2-propenyl ITC, 3-butenyl ITC, and 4-pentenyl ITC (Sarwar et al, Plant Soil, (1998), 201:103-112).

While the invention has been described with reference to details of the illustrated embodiments, these details are not intended to limit the scope of the invention as defined in the appended claims.

The embodiment of the invention in which exclusive property or privilege is claimed is defined as follows:

1. A biologically based test system for the detection of isothiocyanates (ITC) in samples, wherein the test system comprises a genetically modified bacterium or fungus comprising a detectable indicator operably linked to an ITC-responsive promoter, wherein the detectable indicator is induced in the presence of an ITC.

2. The biologically based test system of claim 1, wherein the genetically modified bacterium or fungus is an ITC-resistant bacterium.

3. The biologically based test system of claim 2, wherein the ITC-resistant bacterium is *Pseudomonas fluorescens*.

4. The biologically based test system of claim 1, wherein the detectable indicator is a bioluminescent indicator.

5. The biologically based test system of claim 4, wherein the bioluminescent indicator is encoded by a lux operon or an ilux operon.

6. The biologically based test system of claim 1, wherein the ITC-responsive promoter is a saxA promoter.

7. The biologically based test system of claim 6, wherein the saxA promoter comprises a polynucleotide having a sequence at least 95% identical to SEQ ID NO: 1.

8. The biologically based test system of claim 6, wherein the saxA promoter comprises SEQ ID NO: 1.

9. The biologically based test system of claim 1, wherein the sample comprises a soil sample, a plant sample, or a seed sample.

10. The biologically based test system of claim 1, wherein the ITC is sulforaphane, sulforaphene, metam-sodium, or allyl ITC.

11. The biologically based test system of claim 1, wherein the detectable indicator operably linked to an ITC-responsive promoter is located on a chromosome or on a bacterial plasmid.

12. A genetically modified bacterial or fungal cell for use in a biologically based test system for the detection of ITC from samples, wherein the genetically modified bacterial or fungal cell produces a detectable indicator in the presence of an ITC, and wherein the production of the detectable indicator is induced by an ITC-responsive promoter operably linked to the detectable indicator.

13. The genetically modified bacterial or fungal cell of claim 12, wherein the bacterial or fungal cell is *Pseudomonas fluorescens*.

14. A method for detecting an isothiocyanate in a sample, comprising the steps of:
  i. contacting a sample with the biologically based test system of claim 1;
  ii. incubating the sample mix under conditions allowing for growth of the genetically modified bacterium or fungus of the biologically based test system;
  iii. detecting the presence of the detectable indicator, thus detecting the presence of at least one isothiocyanate.

15. The method of claim 14, wherein the sample is a soil sample, a plant sample, or a seed sample.

16. The method of claim 14, wherein the genetically modified bacterium or fungus is *Pseudomonas fluorescens*.

17. The method of claim 14, wherein the detectable indicator is a bioluminescent indicator.

18. The method of claim 17, wherein the bioluminescent indicator is encoded by a lux operon or an ilux operon.

19. The method of claim 14, wherein the isothiocyanate is sulforaphane, sulforaphene, metam-sodium, or allyl ITC.

* * * * *